United States Patent
Pappas et al.

(10) Patent No.: US 9,463,985 B2
(45) Date of Patent: *Oct. 11, 2016

(54) ALUMINUM SALT CONTAINING HIGH PERCENTAGE OF $AL_{30}$

(75) Inventors: Iraklis Pappas, Pennsauken, NJ (US); John Vaughn, Fair Haven, NJ (US); Long Pan, Cherry Hill, NJ (US)

(73) Assignee: Colgate-Palmolive Company, New York, NY (US)

(*) Notice: Subject to any disclaimer, the term of this patent is extended or adjusted under 35 U.S.C. 154(b) by 163 days.

This patent is subject to a terminal disclaimer.

(21) Appl. No.: 13/882,492

(22) PCT Filed: Oct. 31, 2011

(86) PCT No.: PCT/US2011/058559
§ 371 (c)(1),
(2), (4) Date: Apr. 29, 2013

(87) PCT Pub. No.: WO2012/061280
PCT Pub. Date: May 10, 2012

(65) Prior Publication Data
US 2013/0224140 A1    Aug. 29, 2013

Related U.S. Application Data

(63) Continuation of application No. PCT/US2010/055030, filed on Nov. 2, 2010.

(51) Int. Cl.
*C01F 7/56* (2006.01)
*A61Q 15/00* (2006.01)
(Continued)

(52) U.S. Cl.
CPC . *C01F 7/56* (2013.01); *A61K 8/26* (2013.01); *A61K 8/28* (2013.01); *A61Q 15/00* (2013.01); *C01P 2002/86* (2013.01); *C01P 2002/87* (2013.01); *C02F 1/5245* (2013.01)

(58) Field of Classification Search
None
See application file for complete search history.

(56) References Cited

U.S. PATENT DOCUMENTS

| | | |
|---|---|---|
| 3,979,510 A | 9/1976 | Rubino |
| 3,991,176 A | 11/1976 | Rubino |

(Continued)

FOREIGN PATENT DOCUMENTS

| | | |
|---|---|---|
| CA | 2445924 | 5/2004 |
| CN | 1796283 A | 7/2006 |

(Continued)

OTHER PUBLICATIONS

Kirill L. Shafran, Olivier Deschaume and Carole C. Perry. The static anion exchange method for generation of high purity aluminum polyoxocations and monodisperse aluminium hydroxide nanoparticles. J. Mater. Chem., 2005, 15, 3415-3423.*

(Continued)

*Primary Examiner* — Isaac Shomer
*Assistant Examiner* — Michael P Cohen (57) ABSTRACT

A composition comprising an aluminum chlorohydrate salt, the aluminum chlorohydrate salt having at least 50 mole % $Al_{30}$ polyhydroxyoxoaluminum cation of all polyhydroxyoxoaluminum cations detectable by quantitative $^{27}Al$ NMR within the aluminum chlorohydrate salt, and a buffer. The composition can optionally include zirconium. Also disclosed are a method of making an aluminum salt using an increased molar concentration of a starting aluminum salt with a buffer, a method of reducing perspiration with the aluminum chlorohydrate salt, and a method of treating water with the aluminum chlorohydrate salt.

19 Claims, 6 Drawing Sheets

(51) Int. Cl.
*A61K 8/26* (2006.01)
*A61K 8/28* (2006.01)
*C02F 1/52* (2006.01)

(56) References Cited

U.S. PATENT DOCUMENTS

| | | | |
|---|---|---|---|
| 4,359,456 A * | 11/1982 | Gosling et al. | 424/68 |
| 4,871,525 A | 10/1989 | Giovanniello et al. | |
| 4,900,534 A | 2/1990 | Inward | |
| 5,330,751 A | 7/1994 | Curtin et al. | |
| 5,348,720 A | 9/1994 | Vincenti et al. | |
| 5,358,694 A | 10/1994 | Giovanniello | |
| 5,643,558 A | 7/1997 | Provancal et al. | |
| 5,705,171 A | 1/1998 | Iovanni et al. | |
| 5,955,065 A | 9/1999 | Thong et al. | |
| 5,997,850 A | 12/1999 | Tang et al. | |
| 6,010,688 A | 1/2000 | Shen | |
| 6,042,816 A | 3/2000 | Shen | |
| 6,066,314 A | 5/2000 | Tang et al. | |
| 6,074,632 A | 6/2000 | Shen | |
| 6,136,302 A | 10/2000 | Juneja et al. | |
| 6,149,897 A | 11/2000 | Swaile | |
| 6,245,325 B1 | 6/2001 | Shen | |
| 6,342,210 B1 | 1/2002 | Cai et al. | |
| 6,375,937 B1 | 4/2002 | Chopra et al. | |
| 6,428,778 B1 | 8/2002 | Breker et al. | |
| 6,436,381 B1 | 8/2002 | Carrillo et al. | |
| 6,451,296 B1 | 9/2002 | Li et al. | |
| 6,682,749 B1 | 1/2004 | Potechin et al. | |
| 6,726,901 B2 | 4/2004 | Yin et al. | |
| 6,835,373 B2 | 12/2004 | Kolodzik et al. | |
| 6,902,724 B1 | 6/2005 | Parekh et al. | |
| 6,936,242 B2 | 8/2005 | Elliott et al. | |
| 6,942,850 B2 | 9/2005 | Coe et al. | |
| 6,969,510 B2 | 11/2005 | Holerca et al. | |
| 7,105,691 B2 | 9/2006 | Holerca et al. | |
| 7,189,387 B2 | 3/2007 | Chuah et al. | |
| 7,229,611 B2 | 6/2007 | Zamudio-Tena et al. | |
| 7,256,875 B2 | 8/2007 | Maier et al. | |
| 2004/0101500 A1 | 5/2004 | Ashcroft et al. | |
| 2004/0265255 A1 | 12/2004 | Holerca et al. | |
| 2005/0265939 A1 | 12/2005 | Li | |
| 2006/0153788 A1 | 7/2006 | Swaile et al. | |
| 2006/0204463 A1 | 9/2006 | Tang et al. | |
| 2006/0292098 A1 | 12/2006 | Scavone et al. | |
| 2007/0003499 A1 | 1/2007 | Shen et al. | |
| 2007/0020211 A1 | 1/2007 | Li et al. | |
| 2007/0110687 A1 | 5/2007 | Mattai et al. | |
| 2007/0196302 A1 | 8/2007 | Pratt et al. | |
| 2007/0196303 A1 | 8/2007 | Li et al. | |
| 2008/0131354 A1 | 6/2008 | Li et al. | |
| 2009/0016979 A1 | 1/2009 | Li et al. | |

FOREIGN PATENT DOCUMENTS

| | | |
|---|---|---|
| CN | 101279755 A | 10/2008 |
| EP | 0291334 | 11/1988 |
| GB | 2144992 | 3/1985 |
| WO | WO 2006/046945 | 5/2006 |
| WO | WO 2006/103092 | 10/2006 |
| WO | WO 2006103092 A1 * | 10/2006 |
| WO | WO 2007/004163 | 1/2007 |
| WO | WO 2008/063188 | 5/2008 |
| WO | WO 2009/075678 | 6/2009 |
| WO | WO 2009/076591 | 6/2009 |
| WO | WO 2009075678 A1 * | 6/2009 |

OTHER PUBLICATIONS

Definition of "Aluminum Chlorohydrate" downloaded May 27, 2016, from the site: https://en.wikipedia.org/wiki/Aluminium_chlorohydrate, 4 printed pages.*

Allouche et al., 2000, "Al30: A Giant Aluminum Polycation," Angew Chem. Int. Ed. 39(3):511-514.
Casey, 2006, "Large Aqueous Aluminum Hydroxide Molecules," Chemical Reviews 106(1):1-16.
Casey, 2007, "Reaction Dynamics, Molecular Clusters, and Aqueous Geochemistry," Ann. Rev. Earth Planet Sci. 35:21-46.
Chen et al., 2006, "Evaluation of Al30 Polynuclear Species in Polyaluminum Solutions as Coagulant for Water Treatment," Chemosphere 64:912-918.
Chen et al., 2006, "Effect of Thermal Treatment on the Formation and Transformation of Keggin Al13 and Al30 Species in Hydrolytic Polymeric Aluminum Solutions," Colloids & Surfaces A 292(2-3):110-118.
Chen et al., 2009, "On the Acid-Base Stability of Keggin Al13 and Al30 Polymers in Polyaluminum Coagulants," J. Mater. Sci. 44:3098-3111.
Faust et al., 1998, "Removal of Particulate Matter by Coagulation," Chemistry of Water Treatment, Chapter 6, CRC Press, 2nd ed., pp. 215-270.
Fu et al., 1991, "Aging Processes of Alumina Sol-Gels: Characterization of New Aluminum Polyoxycations by 27AlNMR Spectroscopy," Chem. Mater. 3:602-610.
Huang et al., 2006, "Separation and Purification of Nano-Al13 by UF Method," Colloids & Surfaces A 275:200-208.
International Search Report and Written Opinion in International Application No. PCT/US2011/058559, mailed Apr. 3, 2013.
Mertens et al., 2012, "Polyaluminum chloride with high Al30 content as removal agent for arsenic-contaminated well water," Water Research 46:53-62.
Rosenberg, "Antiperspirant Actives—Enhanced Efficacy Aluminum-Zirconium-Glycine (AZG) Salts" (Cosmetics and Toiletries Worldwide, Fondots, D.C. ed., Hartfordshire UK: Aston Publishing Group, 1993, pp. 252, 254-256).
Shafran et al., 2004, "High-Temperature Speciation Studies of Al-Ion Hydrolysis," Advanced Engineering Materials 6(10):836-839.
Shafran et al., 2005, "The Static Anion Exchange Method for Generation of High Purity Aluminum Polyoxocations and Monodisperse Aluminum Hydroxide Nanoparticles," J. Mater. Chem. 15(33):3415-3423.
Shen et al., 1998, "Synthesis and Speciation of Polyaluminum Chloride for Water Treatment," Environment International 24(8):899-910.
Zhang et al., 2008, "Coagulation Characteristics of Polyaluminum Chlorides PAC-Al30 on Humic Acid Removal from Water," Separation & Purification Tech. 63:642-647.
Shafran et al., 2005, "A systematic investigation of aluminum ion speciation at high temperature. Part 1. Solution studies", Dalton Transactions, Issue 12:2098-2105.
Allouche et al., 2003, "Conversion of Al13 Keggin e into Al30: a reaction controlled by aluminum monomers," Inorg. Chem. Commun. 6:1167-1170.
Bottero, 1980, "Studies of Hydrolyzed Aluminum Chloride Solutions, 1. Nature of Aluminum Species and Composition of Aqueous Solutions," The Journal of Physical Chemistry 84:2933-2939.
Huang et al., 2006, "Separation and Purification of Nano-Al$_{13}$ by UF Method," Colloids and Surfaces A: Physicochem. Eng. Aspects 275:200-208.
International Search Report and Written Opinion in International Application No. PCT/US2010/055030, mailed Sep. 1, 2011.
International Search Report in International Application No. PCT/US2007/087145, mailed Apr. 6, 2009.
International Search Rpeort in International Application No. PCT/US2008/086556, mailed Apr. 6, 2009.
Mertens et al., 2012, "Polyaluminum chloride with high Al30 content as removal agent for arsenic-contaminated well water." Water Research 46:53-62.
Roswell et al., 2000, "Speciation and Thermal Transformation in Alumina Sols: Structures of the Polyhydroxyoxoaluminum Cluster [Al30O8(OH)56(H2O)26]18+ and Its δ-Keggin Moiete," J. Amer. Chem. Soc. 122:3777-3778.
U.S. Appl. No. 12/531,145, filed Sep. 14, 2009.
File History from U.S. Appl. No. 12/531,145 through Oct. 20, 2011.
Written Opinion in International Application No. PCT/US2010/055030, mailed Nov. 28, 2012.

* cited by examiner

ALUMINUM SALT CONTAINING HIGH PERCENTAGE OF AL$_{30}$

CROSS REFERENCE TO RELATED APPLICATIONS

This application is a continuation in part application of PCT/US2010/55030, filed on 2 Nov. 2010, which is incorporated herein by reference.

FIELD OF THE INVENTION

The invention relates to an aluminum salt having a high percentage of Al$_{30}$.

BACKGROUND OF THE INVENTION

Solutions of partially neutralized aluminum are known to contain a variety of hydrolytic Al species. The identity and distribution of these various forms depends on the hydrolysis ratio (i.e. the OH:Al molar ratio), the Al precursor and the choice of the reaction condition.

It is known in the art that such a variety of hydrolytic Al species exists and that it is possible to distinguish large aqueous aluminum hydroxide molecules using spectroscopic methods such as $^{27}$Al NMR which elucidates the structural environment surrounding Al atoms which are embodied in various forms (Casey W H, "Large Aqueous Aluminum Hydroxide Molecules", Chem. Rev. 2006, 106 (1), pages 1 to 16.

There are two regions in a $^{27}$Al NMR spectrum that represent Al nuclei that are octahedrally coordinated (0 ppm-60 ppm) and tetrahedrally coordinated (60 ppm-85 ppm). The octahedral region is exemplified by the hexa-aqua Al species, i.e. monomeric Al, which resonates sharply near 0 ppm. The tetrahedral region is exemplified by resonance near 62.5 ppm from the Al$_{13}$ polyhydroxyoxoaluminum cation. Al$_{13}$ is composed of 12 octahedrally coordinated Al atoms surrounded by one centrally-cited Al atom which is tetrahedrally coordinated. The Al$_{30}$ polyhydroxyoxoaluminum cation is essentially a dimer of the Al$_{13}$ polyhydroxyoxoaluminum cation and contains 2 tetrahedrally sited Al atoms which yield a somewhat broad resonance near 70 ppm. Depending on calibration, the above ppm values can vary. The values for these peaks are approximately where the resonance occurs.

Aluminum salts can be used for many different purposes, which include antiperspirants, and water treatment.

It is theorized that compositions with high amounts of Al$_{30}$ would be more efficacious than compositions with high amounts of Al$_{13}$ at treating water or reducing perspiration. It would be desirable to have an aluminum chlorohydrate salt having a high level of Al$_{30}$ to be used as an antiperspirant or for water treatment.

BRIEF SUMMARY OF THE INVENTION

The present invention provides a composition comprising an aluminum chlorohydrate salt, the aluminum chlorohydrate salt having at least 50 mole % Al$_{30}$ polyhydroxyoxoaluminum cation of all polyhydroxyoxoaluminum cations detectable by quantitative $^{27}$Al NMR within the aluminum chlorohydrate salt, and a buffer.

The present invention also provides a method of making an aluminum chlorohydrate salt comprising:
I) heating an aqueous solution containing a first aluminum salt and a buffer, wherein the first aluminum salt is present in a molar concentration of at least 0.75M, wherein the buffer is an amino acid or betaine and a molar ratio of buffer to aluminum is at least 0.1:1, at a temperature of 50° C. to 100° C. for a period of time of 1 hour to 6 hours to obtain a first aluminum salt solution;
II) adding to the first aluminum salt solution an aqueous solution of an inorganic base to obtain a first aluminum chlorohydrate salt solution having an OH:Al molar ratio of at most 2.6:1, or optionally 2:1 to 2.6:1, and a pH of 2 to 5; and
III) heating the first aluminum chlorohydrate salt solution at a temperature of 50° C. to 100° C. for a period of time of at least 8 hours to obtain a second aluminum chlorohydrate salt solution containing an aluminum chlorohydrate salt having at least 50 mole % Al$_{30}$ polyhydroxyoxoaluminum cation of all polyhydroxyoxoaluminum cations detectable by quantitative $^{27}$Al NMR within the aluminum chlorohydrate salt.

The method can further comprise adding an aqueous solution containing a zirconium compound to the second aluminum chlorohydrate salt solution to thereby obtain an aluminum-zirconium salt solution, optionally having a molar ratio of aluminum to zirconium of 5:1 to 10:1. Optionally, the zirconium compound may be ZrOCl$_2$.8H$_2$O.

The present invention also provides a method for reducing perspiration comprising applying the aluminum chlorohydrate salt or the aluminum chlorohydrate salt made by the method to skin to reduce perspiration.

The present invention also provides a use of the aluminum chlorohydrate salt or the aluminum chlorohydrate salt made by the method to reduce perspiration.

The present invention also provides a method of treating water comprising adding the aluminum chlorohydrate salt or the aluminum chlorohydrate salt made by the method to water.

The present invention also provides for a use of the aluminum chlorohydrate salt or the aluminum chlorohydrate salt made by the method to treat water.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

DETAILED DESCRIPTION OF THE INVENTION

Figure 1A:
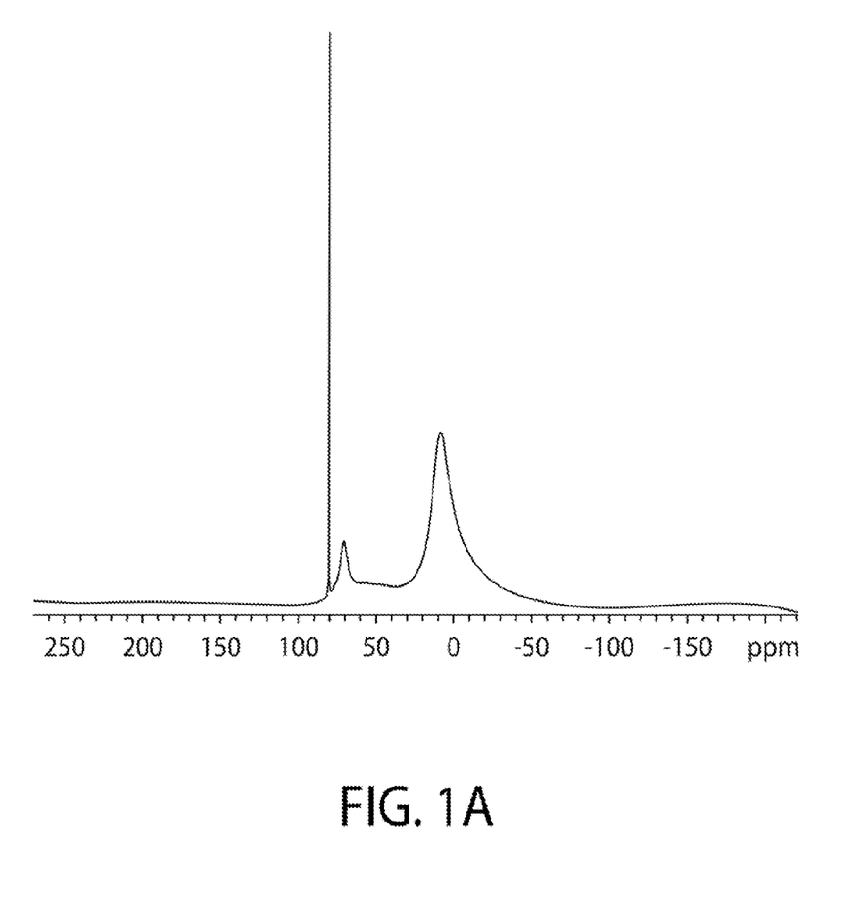
FIG. 1A is a $^{27}$Al NMR of the tetrahedral and octahedral regions for the salt obtained in Example 1.
Figure 1B:
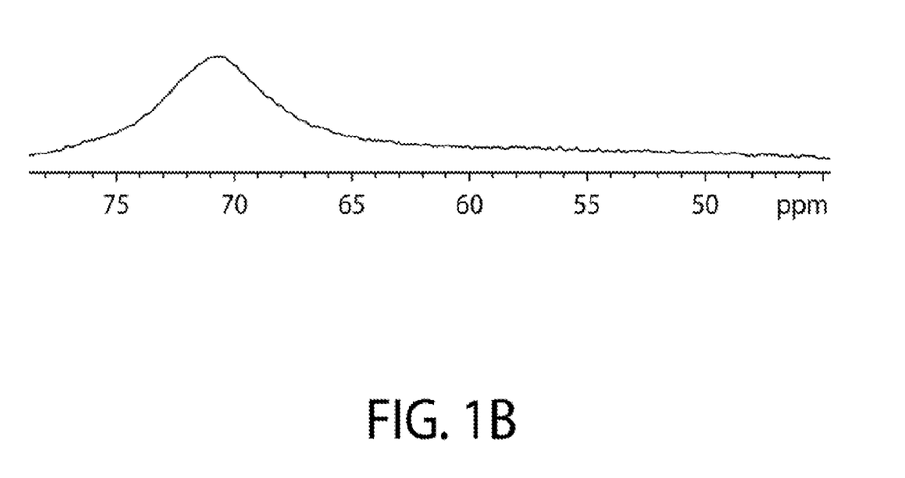
FIG. 1B is the tetrahedral $^{27}$Al NMR region only for this sample.
Figure 1C:
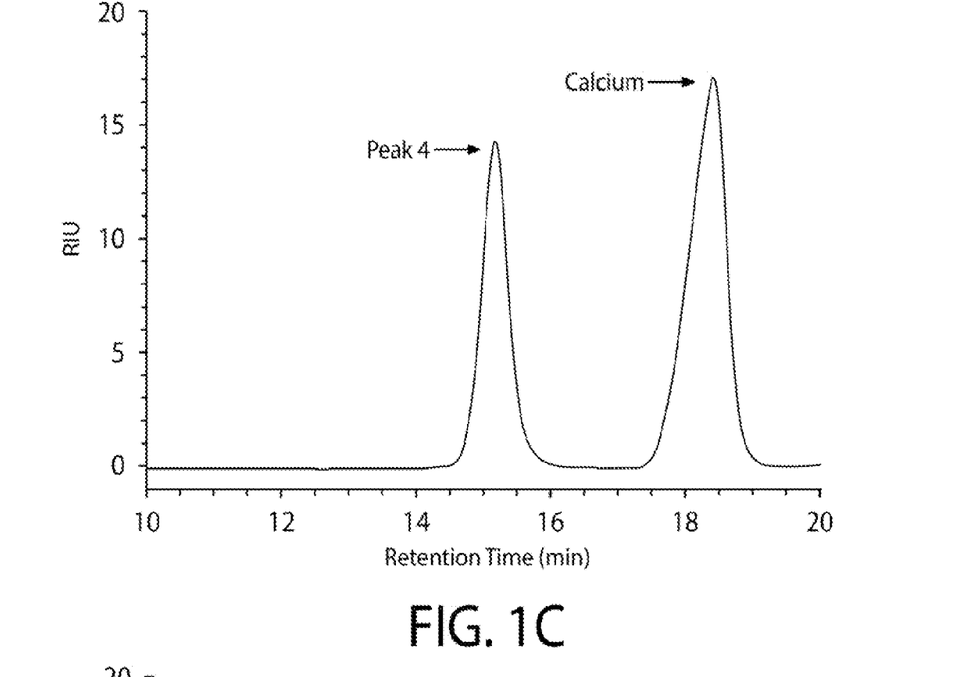
FIG. 1C is the SEC chromatogram for this sample.
Figure 2A:
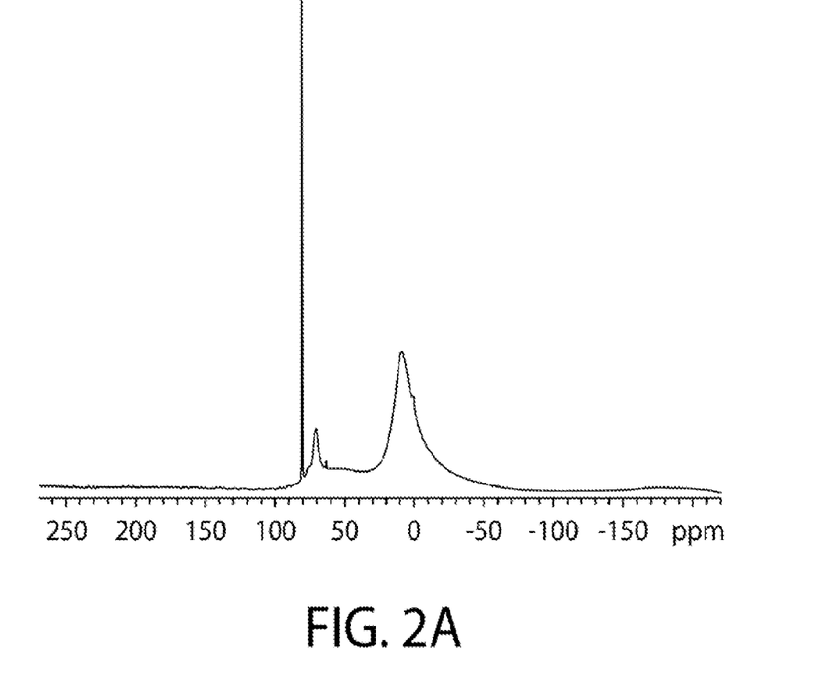
FIG. 2A is a $^{27}$Al NMR of the tetrahedral and octahedral regions for the salt obtained in Example 2.
Figure 2B:
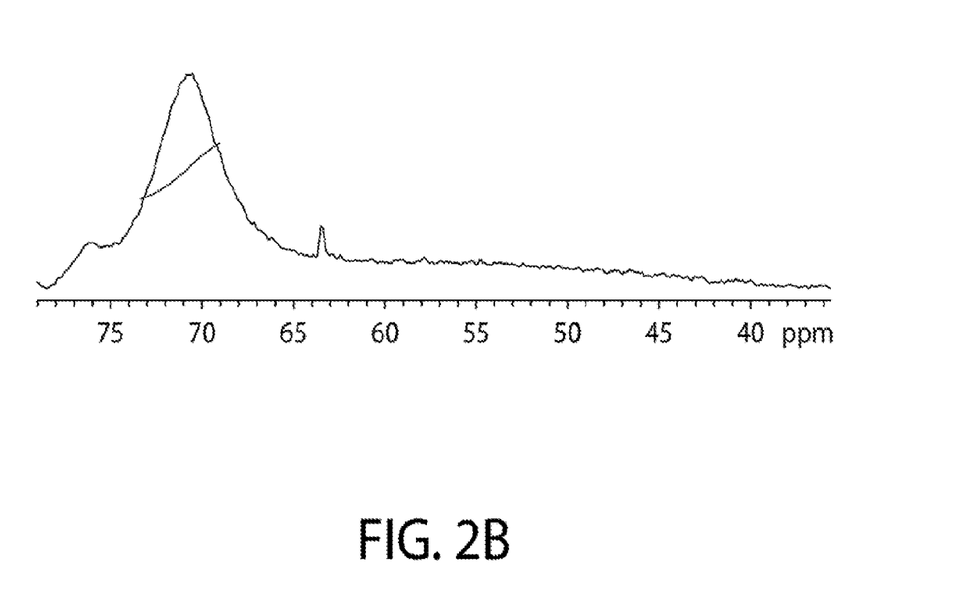
FIG. 2B is the tetrahedral $^{27}$Al NMR region only for this sample.
Figure 2C:
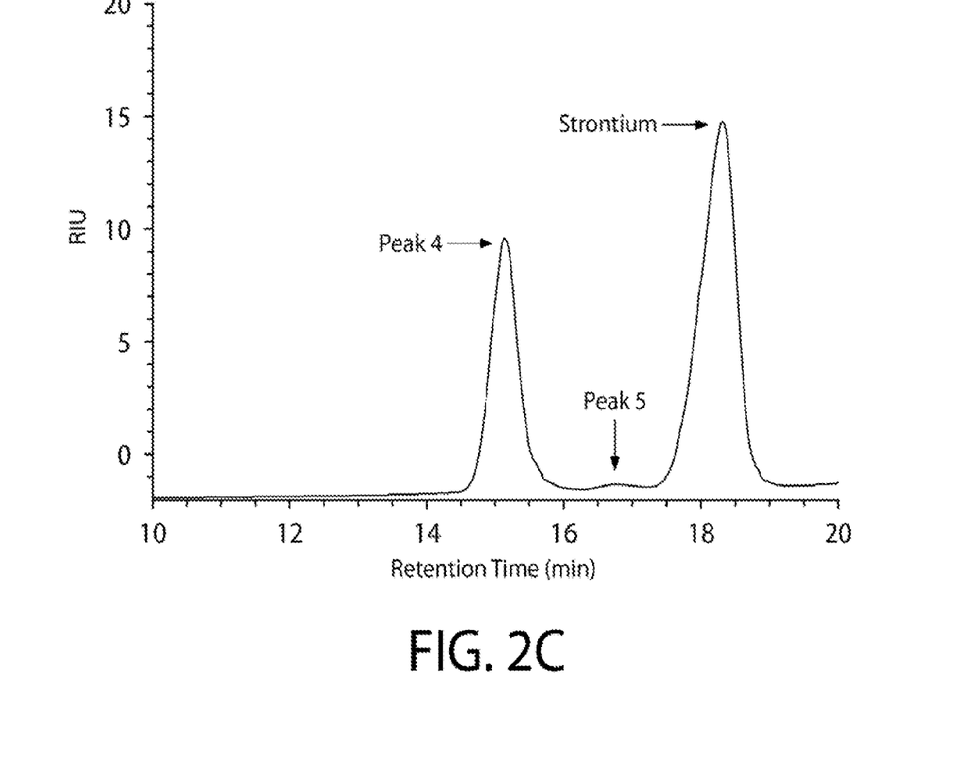
FIG. 2C is the SEC chromatogram for this sample.
Figure 3A:
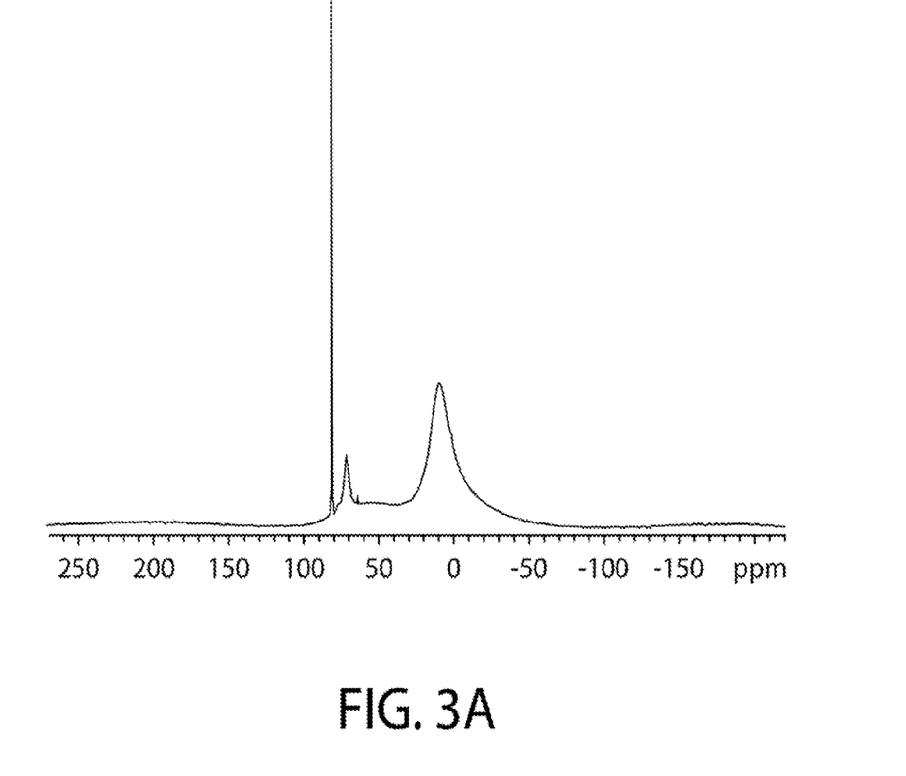
FIG. 3A is a $^{27}$Al NMR of the tetrahedral and octahedral regions for the salt obtained in Example 3.
Figure 3B:
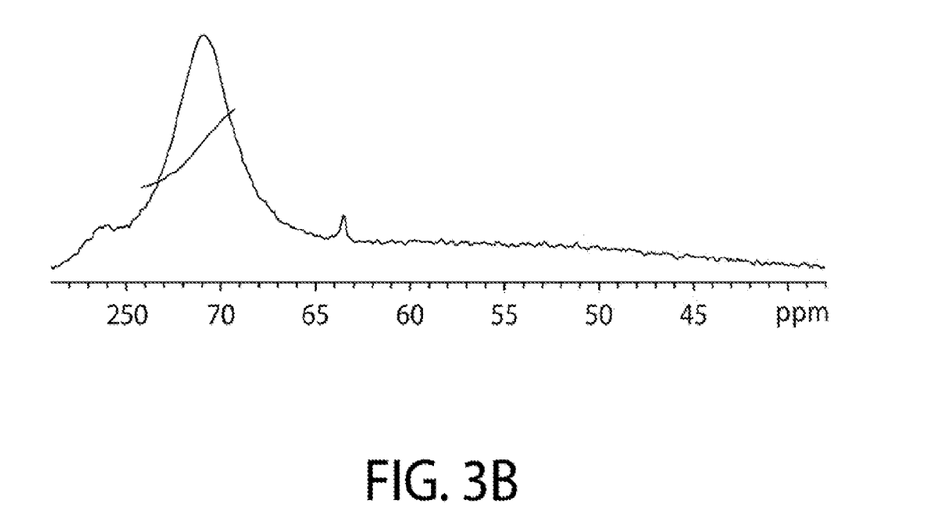
FIG. 3B is the tetrahedral $^{27}$Al NMR region only for this sample.
Figure 3C:
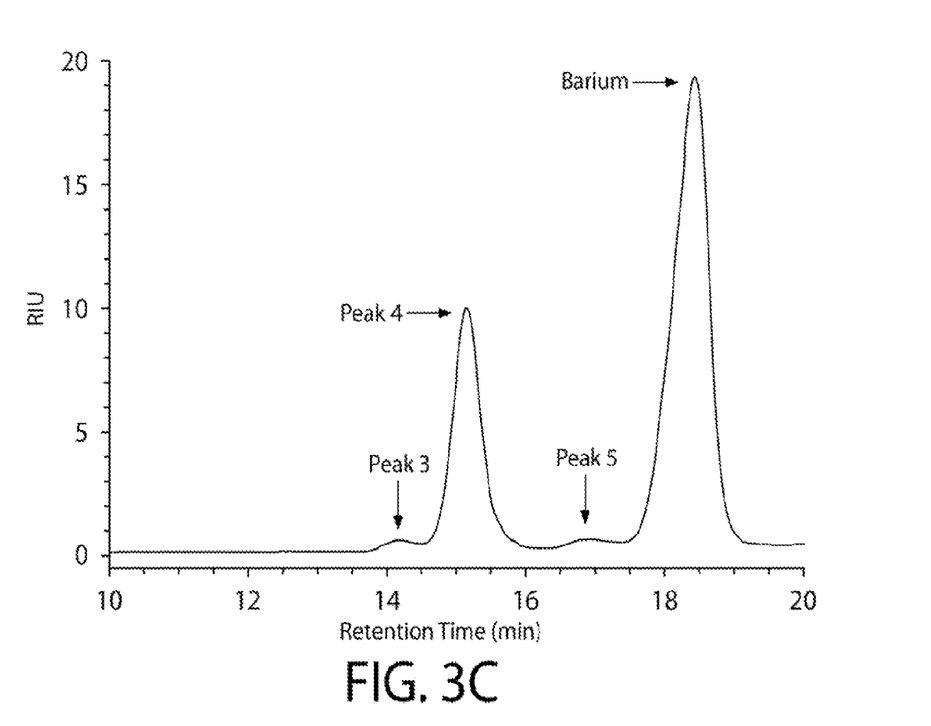
FIG. 3C is the SEC chromatogram for this sample.
Figure 4A:
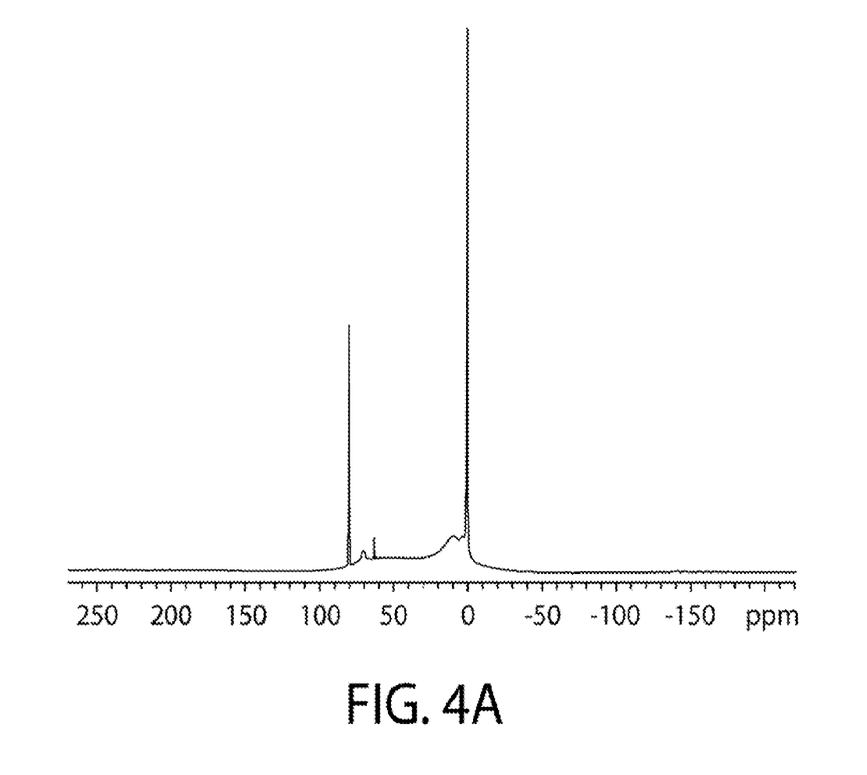
FIG. 4A is a $^{27}$Al NMR of the tetrahedral and octahedral regions for the salt obtained in Comparative Example 2.
Figure 4B:
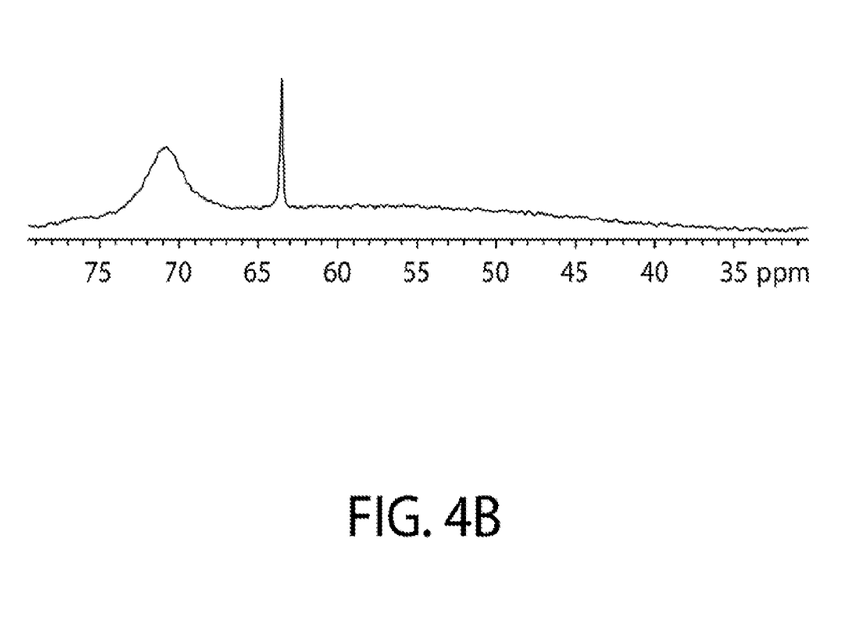
FIG. 4B is the tetrahedral $^{27}$Al NMR region only for this sample.
Figure 4C:
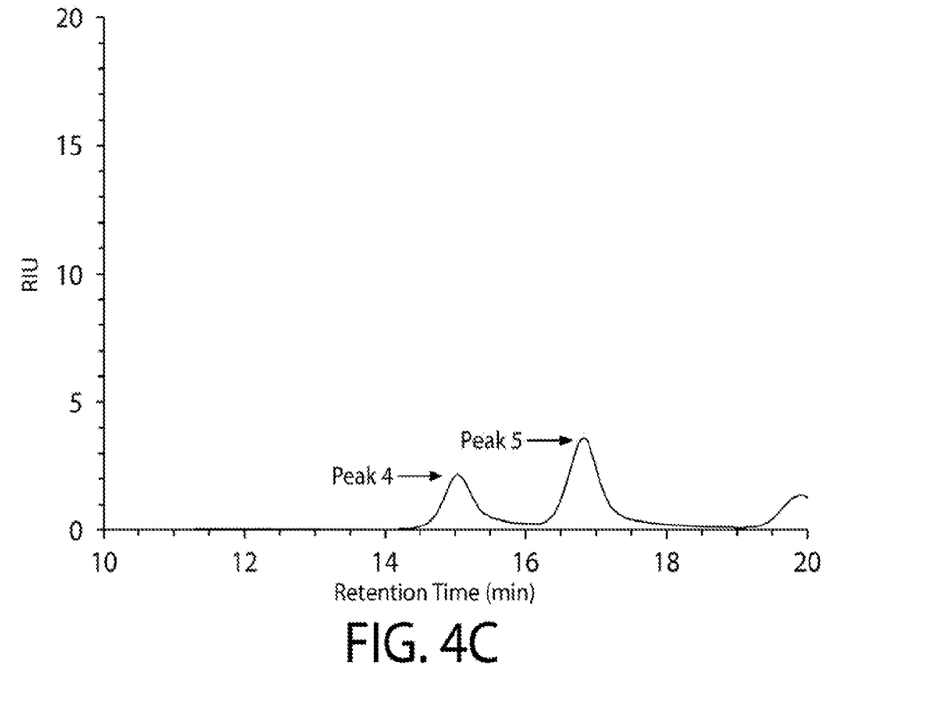
FIG. 4C is the SEC chromatogram for this sample.

The following description of the preferred embodiment(s) is merely exemplary in nature and is in no way intended to limit the invention, its application, or uses.

In previous application PCT/US2010/55030, filed on 2 Nov. 2010, the amounts of the polyhydroxyoxoaluminum cation were determined by qualitative (non-quantitative) $^{27}$Al NMR. In this specification, the amounts of polyhydroxyoxoaluminum cation are determined by quantitative $^{27}$Al NMR, which is described below.

The present invention is directed to an aluminum chlorohydrate salt composition having a high $Al_{30}$ content, and optionally a high SEC peak 4 in aqueous solution. The composition is obtained by a stepwise procedure to neutralize an aluminum salt in a solution (optionally buffered) using inorganic bases. In some embodiments, the aluminum salt compositions obtained by this stepwise procedure include aluminum salts having an aluminum to chloride molar ratio of 0.3:1 to 3:1, optionally, the aluminum salt exhibits a SEC chromatogram having a SEC Peak 4 area of at least 90% of a total area of Peaks 1, 2, 3, 4 and 5 in the SEC chromatogram in aqueous solution. The composition may optionally include zirconium.

The present invention provides a composition comprising an aluminum chlorohydrate salt, the aluminum chlorohydrate salt (i) having an aluminum to chloride molar ratio of 0.3:1 to 3:1; and (ii) having at least 50 mole % $Al_{30}$ polyhydroxyoxoaluminum cation of all polyhydroxyoxoaluminum cations detectable by quantitative $^{27}$Al NMR within the aluminum chlorohydrate salt.

Also provided is a method of making an aluminum chlorohydrate salt comprising:
I) heating an aqueous solution containing a first aluminum salt and a buffer, wherein the first aluminum salt is present in a molar concentration of at least 0.75M, wherein the buffer is an amino acid or betaine and a molar ratio of buffer to aluminum is at least 0.1:1, at a temperature of 50° C. to 100° C. for a period of time of 1 hour to 6 hours to obtain a first aluminum salt solution;
II) adding to the first aluminum salt solution an aqueous solution of an inorganic base to obtain a first aluminum chlorohydrate salt solution having an OH:Al molar ratio of at most 2.6:1, or optionally 2:1 to 2.6:1, and a pH of 2 to 5; and
III) heating the first aluminum chlorohydrate salt solution at a temperature of 50° C. to 100° C. for a period of time of at least 8 hours to obtain a second aluminum chlorohydrate salt solution containing an aluminum chlorohydrate salt having at least 50 mole % $Al_{30}$ polyhydroxyoxoaluminum cation of all polyhydroxyoxoaluminum cations detectable by quantitative $^{27}$Al NMR within the aluminum chlorohydrate salt.

In some embodiments, in step III) the period of time is at least 12 hours, optionally at least 18 hours, at least 24 hours, at least 30 hours, at least 36 hours, at least 42 hours, or at least 48 hours. In one embodiment, the period of time is at least 48 hours.

The high levels of $Al_{30}$ are obtained by a combination of a higher starting molar concentration and including a buffer (for example, glycine). In Chen et al, "Effect of thermal treatment on the formation and transformation of Keggin $Al_{13}$ and $Al_{30}$ species in hydrolytic polymeric aluminum solutions", Colloids and Surfaces A: Physiochem. Eng. Aspects, 292 (2007) pages 110 to 118, as the concentration of the starting aluminum was increased, the amount of $Al_{30}$ decreased. Chen et al. was only able to obtain higher levels of $Al_{30}$ when using a very dilute solution (0.2M). By including a buffer, higher $Al_{30}$ contents can be obtained when starting at higher molar concentrations. This process is more efficient in that dilute solutions in a fixed volume reaction yields less material.

The starting molar concentration of the first aluminum salt is at least 0.75M. The upper limit is only limited by the solubility of the aluminum salt. In other embodiments, the molar concentration is at least 1M, at least 1.25M, at least 1.5M, at least 1.75M, at least 2M, or at least 2.5M. In certain embodiments, even though the molar concentration of the aluminum salt increases, the molar ratios between the aluminum and buffer, the aluminum and OH, and the aluminum and the metal from the base (for example calcium) are maintained the same.

In some embodiments, the aluminum salt has an OH to Al ratio of at most 2.6:1, and in other embodiments 2:1 to 2.6:1, optionally an OH to Al ratio of 2:1 to 2.5:1, or 2.3:1 to 2.5:1.

In some embodiments, there is at least 55 mole % $Al_{30}$ polyhydroxyoxoaluminum cation of all polyhydroxyoxoaluminum cations detectable by quantitative $^{27}$Al NMR, optionally at least 60, at least 65, at least 70, at least 75, at least 80, at least 85, at least 90, or at least 95 mole % in the aluminum chlorohydrate salt. In other embodiments, the $^{27}$Al NMR spectrum has a species distribution including at most 5 mole % $Al_{13}$ polyhydroxyoxoaluminum cation of all polyhydroxyoxoaluminum cations detectable by quantitative $^{27}$Al NMR in the aluminum chlorohydrate salt. In other embodiments, the $^{27}$Al NMR spectrum has a species distribution includes no $Al_{13}$ polyhydroxyoxoaluminum cation of all polyhydroxyoxoaluminum cations detectable by quantitative $^{27}$Al NMR in the aluminum chlorohydrate salt.

The compositions may be made in a variety of ways involving a stepwise procedure to neutralize aluminum salt in solution (optionally buffered) using inorganic basic salts. The procedure generally includes the step of heating an aqueous solution containing an aluminum chloride compound (optionally with a buffer agent) at a temperature of 50° C. to 100° C., optionally 50° C. to 95° C., for a period of time of 1 hour to 6 hours. The heating may be under stirring, such as vigorous stirring, or under reflux. In one such embodiment, an aqueous solution containing an aluminum chloride compound and a buffer agent is heated at a temperature of 75° C. to 95° C. to reflux for a period of time of 2 hours to 4 hours. In one embodiment, the temperature is 95° C. under vigorous stirring for a period of time of 2.5 hours.

To adjust the pH of the aluminum salt solution, an aqueous solution of an inorganic base is added to the heated solution to thereby obtain a pH adjusted aluminum salt solution having a hydroxide to aluminum molar ratio of 1:1 to 4:1, and a pH of 2 to 5. In one such embodiment, the hydroxide to aluminum molar ratio of 2:1 to 3:1. In another such embodiment, the hydroxide to aluminum molar ratio is 2.1:1 to 2.6:1.

In one embodiment, the inorganic base can be at least one base chosen from metal hydroxides, calcium hydroxide, strontium hydroxide, sodium hydroxide, barium hydroxide, metal oxides, calcium oxide, strontium oxide, barium oxide, metal carbonates, calcium carbonate, strontium carbonate, barium carbonate, yttrium hydroxide, yttrium oxide, and yttrium carbonate.

Optionally, a buffer can be included. Buffers that can be used can be chosen from amino acids, such as glycine, and betaine, such as betaine monohydrate (trimethylglycine) or betaine hydrochloride (trimethylglycine hydrochloride). The buffer to aluminum molar ratio in certain embodiments can be at least 0.1:1, or 0.1:1 to 3:1. In another embodiment, the buffer to aluminum molar ratio is 0.1:1 to 2:1.

In one embodiment, the inorganic base is calcium hydroxide. In one such embodiment, the addition of calcium hydroxide provides an aqueous solution having a $Ca(OH)_2$: glycine molar ratio of at least 0.1:1.

In some embodiments, the buffer is glycine, the inorganic base is calcium hydroxide, and the first aluminum chlorohydrate salt solution has an OH to Al molar ratio of 2.0:1 to 2.5:1 or 2.1:1 to 2.5:1.

When a buffer is absent, significant Peak 3 species in the SEC chromatogram begin to form when the total Al concentration is above 0.2M. When a buffer is present, the total Al concentration can reach up to 2.5M while maintaining a predominant Peak 4 in the SEC chromatogram. In one embodiment, an aqueous aluminum chloride salt solution is buffered with glycine and held at 50° C. to 95° C. under vigorous stirring for a period time of 1 to 6 hours. To the heated solution, an aqueous solution of an inorganic base is added dropwise over a period of time of 1 to 3 hours while maintaining the aluminum-glycine solution at 50° C. to 95° C. under vigorous stirring. In one such embodiment, the solution has a glycine to aluminum molar ratio of 1.5. In another such embodiment, the solution has a glycine to aluminum molar ratio of 0.5.

In some embodiments, a zirconium salt may also be added to the pH adjusted aluminum salt solution. In one other such embodiment, the molar ratio of Al:Zr is 5:1 to 10:1. The zirconium salt may be $ZrOCl_2 \cdot 8H_2O$. In one such embodiment, the molar ratio of Al:Zr is 8. In another such embodiment, the molar ratio of Al:Zr is 7. In one other such embodiment, the molar ratio of Al:Zr is 9.

For the above methods, the aluminum chloride salt and inorganic base may be obtained from a variety of sources. In one embodiment, the aluminum chloride salt includes aluminum trichloride, aluminum chlorohexahydrate and aluminum dichlorohydrate. In one such embodiment, the aluminum chloride salt is aluminum chlorohexahydrate.

Size exclusion chromatography ("SEC") or gel permeation chromatography ("GPC") are methods frequently used for obtaining information on polymer distribution in aluminum salt solutions. With appropriate chromatographic columns, generally five distinctive groups of polymer species can be detected in commercial ACH and ZAG complexes appearing in a chromatogram as peaks 1, 2, 3, 4 and a peak known as "5,6", referred to hereinafter as Peak 5. Peak 1 is the larger Zr species (greater than 60 Angstroms). Peaks 2 and 3 are larger aluminum species. Peak 4 is smaller aluminum species (aluminum oligomers, or small aluminum clusters) and has been correlated with enhanced efficacy for both Al and Al/Zr salts. Peak 5 is the smallest aluminum species. Various analytical approaches for characterizing the peaks of ACH and various types of ZAG actives are found in "Antiperspirant Actives—Enhanced Efficacy Aluminum-Zirconium-Glycine (AZG) Salts" by Dr. Allan H. Rosenberg (Cosmetics and Toiletries Worldwide, Fondots, D. C. ed., Hertfordshire, UK: Aston Publishing Group, 1993, pages 252, 254-256). Size Exclusion Chromatography (SEC) chromatography is the traditional method used for elucidating the distribution of these Al species. Conventional SEC physically separates Al species into domains which are subsequently measured using a concentration detector. It is generally recognized that at least five domains of Al species can be differentiated by size-exclusion chromatography.

These domains are commonly referred to Peak 1, Peak 2 . . . Peak 5, where increasing peak number indicates smaller relative size of the eluting species. As discussed above, Peak 4 and Peak 5 have been implicated as highly efficacious Al domains. Monomeric Al, which is undesirable because of its acidity, is known to elute under Peak 5.

The design of modern aluminum salts aims at actives with high levels of low molecular weight Al and Zr species, which is reflected in a SEC trace that has intense Peak 4 and low Peaks 1, 2, and 3, and optionally low Peak 5. Throughout the present study, the levels of the species corresponding to these peaks are estimated based on the following ratios (or percentages):

$$f_{Pi} = \frac{Pi}{\sum Pj} \; i = 1, 2, 3, 4, 5; j = 2, 3, 4, 5$$

where $f_{Pi}$ is the fraction of peak i, and Pi or Pj are the intensity of peaks Pi or Pj, respectively. The amount of low molecular weight Al species will be correlated with the fraction, $f_{P4}$, or percentage, $f_{P4} \times 100$, of SEC-Peak 4. In brief, a preferred aluminum salt would have a very low $f_{P1}$, $f_{P2}$, $f_{P3}$, and/or $f_{P5}$, and a high $f_{P4}$.

The present invention provides for aluminum compositions and/or aluminum-zirconium salt compositions having high levels of low molecular weight Al and Zr species. The polymerization of the aluminum salt in aqueous solutions and the correspondent gelation process were followed by monitoring the molecular weight profile of the polyoxohalides in time by SEC. The relative retention time ("Kd") for each of these peaks varies depending on the experimental conditions, but the peaks remain relative to each other. The SEC data for the examples was obtained using an SEC chromatogram using the following parameters: Waters® 600 analytical pump and controller, Rheodyne® 77251 injector, Protein-Pak® 125 (Waters) column, Waters 2414 Refractive Index Detector. 5.56 mM nitric acid mobile phase, 0.50 ml/min flow rate, 2.0 microliter injection volume. Data was analyzed using Water® Empower software (Waters Corporation, Milford, Mass.). The concentration of the aluminum salt in aqueous solution does not affect the retention time in the machine. In this specification, the SEC chromatogram is measured using an aqueous solution of the aluminum salt.

In some embodiments, the aluminum chlorohydrate salt has a SEC Peak 4 area of at least 95% of a total area of Peaks 1, 2, 3, 4 and 5 in the SEC chromatogram. In some embodiments, the aluminum chlorohydrate salt has a SEC Peak 3 area of less than 5% of a total area of Peaks 1, 2, 3, 4 and 5 in the SEC chromatogram, and preferably the aluminum chlorohydrate salt has no SEC Peak 3 area in the SEC chromatogram. In some embodiments, the aluminum chlorohydrate salt has a SEC Peak 5 area of less than 5% of a total area of Peaks 1, 2, 3, 4 and 5 in the SEC chromatogram. In some embodiments, the aluminum salt has a SEC Peak 4 area of 95 to 100%, no SEC Peak 3 area, and a SEC Peak 5 area of from 0 to 5% of a total area of Peaks 1, 2, 3, 4 and 5 in the SEC chromatogram.

In certain embodiments, the ratio of Peak 4 to Peak 3 is at least 8, 9, 10, 11, 12, 13, 14, 15, 16, 17, 18, 19, 20, 25, 30, 35, 40, 45, 50, 60, 70, 80, 90, 100, or any number up to infinity. Preferably, Peak 3 is so low as to be undetectable.

In one embodiment, an aluminum salt and/or aluminum-zirconium salt, in aqueous solution, exhibit a SEC profile wherein the SEC Peak 4 to Peak 3 intensity ratio is even as high as infinity, because the Peak 3 is undetectable. In some embodiments, the percentage of SEC Peak 4 of a total area of Peaks 1, 2, 3, 4 and 5 in the SEC chromatogram is: at least at least 90%; at least 95%, or 95 to 100%. In another such embodiment, the SEC Peak 4 area is 100%.

In another embodiment, the aluminum salt and/or the aluminum-zirconium salt, in aqueous solution, exhibits a SEC profile which exhibits low percentage of SEC Peak 3. In such embodiments, the composition has the percentage of SEC Peak 3 area of a total area of Peaks 1, 2, 3, 4 and 5 in the SEC chromatogram is: less than 5%; less than 2%; less than 1%; less than 0.9%; less than 0.8%; less than 0.7%; less than 0.6%; of less than 0.5%; less than 0.4%; less than 0.3%; less than 0.2%; or less than 0.1%. In another such embodiment, the composition has no SEC Peak 3 area.

In another embodiment, the aluminum salt and/or the aluminum-zirconium salt, in aqueous solution, exhibits a SEC profile which exhibits low percentages of SEC Peak 5. In such embodiments, the percentage of SEC Peak 5 area of a total area of Peaks 1, 2, 3, 4 and 5 in the SEC chromatogram is: less than 5%; or less than 1%. In another such embodiment, the composition has no SEC Peak 5 area.

In other embodiments, the aluminum salt and/or the aluminum-zirconium salt, in aqueous solution, exhibits a SEC profile which exhibits a low percentage of SEC Peak 1 and a low percentage of SEC Peak 2. In such embodiments, the percentage of SEC Peak 1 area of a total area of Peaks 1, 2, 3, 4 and 5 in the SEC chromatogram is less than 5%; less than 2%; or less than 1%, or the salt has no SEC Peak 1 area. In other embodiments, the percentage of SEC Peak 2 area of a total area of Peaks 1, 2, 3, 4 and 5 in the SEC chromatogram is less than 5%; less than 2% or less than 1%; or the salt has no SEC Peak 2 area. Preferably, the salt has no Peak 1 area and no Peak 2 area. More preferably, the salt has no Peak 1 area, no Peak 2 area and no Peak 3 area. Yet more preferably, the salt has no Peak 1 area, no Peak 2 area, no Peak 3 area and no Peak 5 area.

The aluminum and/or aluminum-zirconium salts may be used in a variety of antiperspirant products. If the product is used as a solid powder, the size of the particles of antiperspirant active of the invention can be any desired size, and may include conventional sizes such as in the range of 2 to 100 microns, with selected grades having an average particle size of 30-40 microns; finer sized grades having an average particle size distribution of 2-10 microns with an average size of 7 microns as made by a suitable dry-grinding method; and micronized grades having an average particle size of less than or equal to 2 microns, or less than or equal to 1.5 microns.

The compositions of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions. These antiperspirant actives can be used as the antiperspirant active in any antiperspirant composition.

The aluminum salt can be used to treat water, and in particular wastewater. The wastewater can be type of wastewater including, but not limited to, municipal wastewater or wastewater from industrial processes. When added to water, the aluminum salt can coagulate suspended solids so that they can settle out or be filtered out. The aluminum salt can also reduce total organic carbon content, remove phosphates, lower chemical oxygen demand, and lower biological oxygen demand. The aluminum salt can be used according to any of the known methods for treating water with an aluminum salt.

Quantitative NMR Method

The moles of aluminum in each sample are first determined by elemental analysis. Any type of elemental analysis can be used, such as Inductively Coupled Plasma—Optical Emission Spectrometry (ICP-OES) or atomic absorption spectroscopy.

The NMR instrument is calibrated with $Al(NO_3)_3$ (primary standard) and $NaAlO_2$ (secondary standard) of known concentrations. The NMR uses a coaxial tube inserted within the primary NMR tube.

$^{27}Al$ NMR is measured on a Varian 400-1 instrument. The following parameters are used for the instrument: equilibrate at 90 C for 20 mins, sfrq: 104.177 MHz, np: 17664, fn: 64 k, pw: 9.4 us, dl: 1 s, LB: 10.0 Hz, sw: 51.1 k, nt: 2000.

The molar percentages of $Al_{13}$ and $Al_{30}$ are determined using the following equations:

$$\frac{13 \times \text{Moles } Td\ Al_{13}}{\text{Moles Al from Elemental Analysis}} \times 100 = \text{mole } \%\ Al_{13}$$

$$\frac{15 \times \text{Moles } Td\ Al_{30}}{\text{Moles Al from Elemental Analysis}} \times 100 = \text{mole } \%\ Al_{30}$$

The present invention is exemplified by the following non-limiting Examples.

EXAMPLES

Example 1

18.02 g of glycine is added to 182.27 g of an aqueous solution of 1.25 M $AlCl_3$. The mixture is heated to 95° C. for 1 hour with stirring. 38.72 g of a 48.34 weight % $Ca(OH)_2$ paste is added over 1 hour with vigorous stirring followed by addition of 20 ml of water. Final [Al] is 1M. Stirring is reduced and heating is continued for 48 hours. Sample is diluted to 0.2M [Al] for analysis.

Example 2

18.02 g of glycine is added to 182.27 g of an aqueous solution of 1.25 M $AlCl_3$. The mixture is heated to 95° C. for 1 hour with stirring. 63.77 g of crystalline $Sr(OH)_2$ is added over 1 hour with vigorous stirring followed by addition of 20 ml of water. Final [Al] is 1M. Stirring is reduced and heating is continued for 48 hours. Sample is diluted to 0.2M [Al] for analysis.

Example 3

18.02 g of glycine is added to 182.27 g of an aqueous solution of 1.25 M $AlCl_3$. The mixture is heated to 95° C. for 1 hour with stirring. 75.71 g of crystalline $Ba(OH)_2$ is added over 1 hour with vigorous stirring followed by addition of 20 ml of water. Final [Al] is 1M. Stirring is reduced and heating is continued for 48 hours. Sample is diluted to 0.2M [Al] for analysis.

Comparative Example 1

9.38 g of glycine is added to 200 ml of a 0.5 M solution of $AlCl_3$ and heated to 95° C. with stirring. To this solution is added 250 ml of a 0.492 M solution of $Ca(OH)_2$ over a 1 hour period. Stirring is reduced and heating is continued for an additional 1 hour. Final [Al] is 0.22 M. See FIG. 5 in WO2009/076591 for the SEC graph.

Comparative Example 2

182.27 g of an aqueous solution that is 1.25M AlCl₃ is heated to 95° C. for 1 hour with stirring. 39.19 g of a 48.98 weight % NaOH solution is added over 1 hour with vigorous stirring followed by addition of 20 ml of water. Final [Al] is 1M. Stirring is reduced and heating continued for 48 hours. Sample is diluted to 0.2M [Al] for analysis.

The examples above are analyzed for the amount of $Al_{30}$ by quantitative NMR and qualitative NMR. Qualitative NMR calculation is described in PCT/US2010/55030. The results are shown in the table below.

| Example | Mole % $Al_{30}$ by Quantitative NMR | % Al30 by Qualitative NMR |
|---|---|---|
| Example 1 | 82.57 | 100 |
| Example 2 | 66.89 | 86.96 |
| Example 3 | 69.74 | 86.27 |
| Comparative 1 | 42.49 | 73.25 |
| Comparative 2 | 31.98 | 77.02 |

The Examples and Comparative Examples collectively show that the use of the buffer, such as glycine and higher starting molar concentration combined with a prolonged reaction time at elevated temperature, typically more than 24 hours or more than 48 hours, can cause conversion of a substantial proportion of, even all of, the $Al_{13}$ polyhydroxyoxoaluminum cation into the $Al_{30}$ polyhydroxyoxoaluminum cation, without causing the creation of any SEC-Peak 3 aluminum-containing molecules. The SEC chromatogram of the resultant aluminum salt can exhibit a Peak 4 area of at least 90% of a total area of Peaks 1, 2, 3, 4 and 5 in the SEC chromatogram, and with zero detectable Peak 3 and Peak 5 species, as well as zero detectable Peak 1 and Peak 2 species. The conversion of the $Al_{13}$ polyhydroxyoxoaluminum cation into the $Al_{30}$ polyhydroxyoxoaluminum cation does not, per se, increase the Peak 4 area because both the $Al_{13}$ polyhydroxyoxoaluminum cation and the $Al_{30}$ polyhydroxyoxoaluminum cation elute under Peak 4 when the aluminum salt is subjected to SEC chromatography. The $Al_{30}$ polyhydroxyoxoaluminum cation, however, has a higher stability than the $Al_{13}$ polyhydroxyoxoaluminum cation.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A composition comprising an aluminum chlorohydrate salt, the aluminum chlorohydrate salt having at least 50 mole % $Al_{30}$ polyhydroxyoxoaluminum cation of all polyhydroxyoxoaluminum cations detectable by quantitative $^{27}Al$ NMR within the aluminum chlorohydrate salt, and a buffer, wherein the $^{27}Al$ NMR spectrum has a species distribution including at most 5 mole % $Al_{13}$ polyhydroxyoxoaluminum cation of all polyhydroxyoxoaluminum cations detectable by quantitative $^{27}Al$ NMR in the aluminum chlorohydrate salt, and wherein the aluminum chlorohydrate salt having at least 50 mole % $Al_{30}$ polyhydroxyoxoaluminum cation is obtained by:
   I) heating an aqueous solution containing a first aluminum salt and a buffer, wherein the first aluminum salt is present in a molar concentration of at least 0.75M, wherein the buffer is an amino acid or betaine and a molar ratio of buffer to aluminum is at least 0.1:1, at a temperature of 50° C. to 100° C. for a period of time of 1 hour to 6 hours to obtain a first aluminum salt solution;
   II) adding to the first aluminum salt solution an aqueous solution of an inorganic base to obtain a first aluminum chlorohydrate salt solution having an OH:Al molar ratio of at most 2.6:1, or optionally 2:1 to 2.6:1, and a pH of 2 to 5; and
   III) heating the first aluminum chlorohydrate salt solution at a temperature of 50° C. to 100° C. for a period of time of at least 8 hours to obtain a second aluminum chlorohydrate salt solution containing an aluminum chlorohydrate salt having at least 50 mole % $Al_{30}$ polyhydroxyoxoaluminum cation of all polyhydroxyoxoaluminum cations detectable by quantitative $^{27}Al$ NMR within the aluminum chlorohydrate salt.

2. The composition of claim 1, wherein there is at least 55 mole % $Al_{30}$ polyhydroxyoxoaluminum cation of all polyhydroxyoxoaluminum cations detectable by quantitative $^{27}Al$ NMR in the aluminum chlorohydrate salt.

3. The composition of claim 1, wherein the aluminum chlorohydrate salt exhibits a SEC chromatogram having a SEC Peak 4 area of at least 90% of a total area of Peaks 1, 2, 3, 4 and 5 in the SEC chromatogram.

4. The composition of claim 1, wherein the $^{27}Al$ NMR spectrum has a species distribution including no $Al_{13}$ polyhydroxyoxoaluminum cation of all polyhydroxyoxoaluminum cations detectable by quantitative $^{27}Al$ NMR of the aluminum chlorohydrate salt.

5. The composition of claim 1, wherein the aluminum chlorohydrate salt has an aluminum to chloride molar ratio of 0.3:1 to 3:1.

6. The composition of claim 1, wherein, the aluminum chlorohydrate salt has an OH to Al ratio of 2:1 to 2.5:1.

7. The composition of claim 1, wherein the buffer is at least one buffer chosen from an amino acid and betaine.

8. The composition of claim 7, wherein the buffer is an amino acid and a molar ratio of amino acid to aluminum is at least 0.1.

9. The composition of claim 1, wherein the buffer is glycine.

10. The composition of claim 1, wherein the buffer is glycine and is present in a glycine to aluminum molar ratio of 0.1:1 to 2:1, and the aluminum chlorohydrate salt has an OH to Al ratio of 2:1 to 2.5:1, and the aluminum chlorohydrate salt has an aluminum to chloride molar ratio of 0.3:1 to 3:1.

11. The composition of claim 10, wherein the composition has no SEC Peak 3 area in the SEC chromatogram.

12. The composition of claim 1, wherein the composition has a SEC Peak 4 area of at least 95% of a total area of Peaks 1, 2, 3, 4 and 5 in the SEC chromatogram.

13. The composition of claim 1, wherein the composition has a SEC Peak 3 area of less than 5% of a total area of Peaks 1, 2, 3, 4 and 5 in the SEC chromatogram.

14. The composition of claim 13, wherein the composition has no SEC Peak 5 area in the SEC chromatogram.

15. The composition of claim 1, wherein the composition has a SEC Peak 5 area of less than 5% of a total area of Peaks 1, 2, 3, 4 and 5 in the SEC chromatogram.

16. The composition of claim 1, wherein the composition has a SEC Peak 4 area of 95 to 100%, no SEC Peak 3 area, and a SEC Peak 5 area of from 0 to 5% of a total area of Peaks 1, 2, 3, 4 and 5 in the SEC chromatogram.

17. The composition of claim 1, wherein the composition further comprises zirconium, optionally having a molar ratio of aluminum to zirconium of 5:1 to 10:1.

18. A method for reducing perspiration comprising applying an aluminum chlorohydrate salt of claim 1 to skin to reduce perspiration.

19. A method for treating water comprising adding an aluminum chlorohydrate salt of claim 1 to water.

* * * * *